US012636066B2

(12) United States Patent
Drochner et al.

(10) Patent No.: US 12,636,066 B2
(45) Date of Patent: May 26, 2026

(54) SURGICAL INSTRUMENTS, SYSTEMS, AND METHODS INCORPORATING ULTRASONIC AND ELECTROSURGICAL FUNCTIONALITY

(71) Applicant: Covidien LP, Mansfield, MA (US)

(72) Inventors: Thomas E. Drochner, Longmont, CO (US); Matthew S. Cowley, Frederick, CO (US); Kenlyn Bonn, Lakewood, CO (US); James R. Fagan, Erie, CO (US); Michael B. Lyons, Boulder, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 328 days.

(21) Appl. No.: 18/281,940

(22) PCT Filed: Mar. 10, 2022

(86) PCT No.: PCT/IB2022/052156
§ 371 (c)(1),
(2) Date: Sep. 13, 2023

(87) PCT Pub. No.: WO2022/195412
PCT Pub. Date: Sep. 22, 2022

(65) Prior Publication Data
US 2024/0156512 A1      May 16, 2024

Related U.S. Application Data

(60) Provisional application No. 63/162,926, filed on Mar. 18, 2021.

(51) Int. Cl.
A61B 18/14      (2006.01)
A61B 18/00      (2006.01)
A61B 18/12      (2006.01)

(52) U.S. Cl.
CPC .... *A61B 18/14* (2013.01); *A61B 2018/00059* (2013.01); *A61B 2018/00184* (2013.01);
(Continued)

(58) Field of Classification Search
CPC ........... A61B 2018/00184; A61B 2018/00964; A61B 2018/00994; A61B 2018/1253;
(Continued)

(56) References Cited

U.S. PATENT DOCUMENTS

| | | | |
|---|---|---|---|
| 5,190,517 A | 3/1993 | Zieve et al. | |
| 5,312,329 A | 5/1994 | Beaty et al. | |

(Continued)

OTHER PUBLICATIONS

International Search Report and Written Opinion received for PCT Patent Application No. PCT/IB2022/052156, mailed on Aug. 16, 2022, 18 pages.

(Continued)

*Primary Examiner* — Bradford C. Blaise

(57) ABSTRACT

An end effector assembly of a surgical instrument includes an ultrasonic blade. A jaw member is movable relative to the ultrasonic blade from a spaced-apart position to an approximated position. The jaw member includes a structural body. The structural body defines a first side facing the ultrasonic blade and a second side facing away from the ultrasonic blade. A jaw liner is engaged with the first side of the structural body such that the jaw liner contacts the ultrasonic blade when the jaw member is in the approximated position. An electrode is engaged with the second side of the structural body. The electrode is adapted to connect to a source of electrosurgical energy. The electrode defines a first portion and a second portion. The first portion of the electrode is in contact with the structural body and the second portion of the electrode tapers to a pointed edge.

13 Claims, 7 Drawing Sheets

(52) U.S. Cl.
CPC .............. *A61B 2018/00964* (2013.01); *A61B 2018/00994* (2013.01); *A61B 2018/1253* (2013.01); *A61B 2018/1405* (2013.01); *A61B 2018/1475* (2013.01)

(58) Field of Classification Search
CPC ........ A61B 2018/1405; A61B 18/1442; A61B 18/1445; A61B 18/1447; A61B 2018/145; A61B 2018/1452; A61B 2018/1455; A61B 2018/1475
See application file for complete search history.

(56) References Cited

U.S. PATENT DOCUMENTS

| | | | |
|---|---|---|---|
| 5,443,463 | A | 8/1995 | Stern et al. |
| 6,251,110 | B1 | 6/2001 | Wampler |
| 6,257,241 | B1 | 7/2001 | Wampler |
| 6,416,486 | B1 | 7/2002 | Wampler |
| 6,562,032 | B1 | 5/2003 | Ellman et al. |
| 6,648,839 | B2 | 11/2003 | Manna et al. |
| 6,736,814 | B2 | 5/2004 | Manna et al. |
| 6,902,536 | B2 | 6/2005 | Manna et al. |
| 7,717,913 | B2 | 5/2010 | Novak et al. |
| 7,717,915 | B2 | 5/2010 | Miyazawa |
| 7,905,881 | B2 | 3/2011 | Masuda et al. |
| 7,909,824 | B2 | 3/2011 | Masuda et al. |
| 8,048,074 | B2 | 11/2011 | Masuda |
| 8,147,488 | B2 | 4/2012 | Masuda |
| 8,382,748 | B2 | 2/2013 | Geisel |
| 8,663,220 | B2 | 3/2014 | Wiener et al. |
| 8,663,223 | B2 | 3/2014 | Masuda et al. |
| 8,773,001 | B2 | 7/2014 | Wiener et al. |
| 9,039,690 | B2 | 5/2015 | Kersten et al. |
| 9,326,787 | B2 | 5/2016 | Sanai et al. |
| 9,364,279 | B2 | 6/2016 | Houser et al. |
| 9,592,072 | B2 | 3/2017 | Akagane |
| 9,681,912 | B2 | 6/2017 | Tsubuku et al. |
| 9,700,366 | B2 | 7/2017 | Paulus |
| 9,757,142 | B2 | 9/2017 | Shimizu |
| 9,764,164 | B2 | 9/2017 | Wiener et al. |
| 9,808,305 | B2 | 11/2017 | Hareyama et al. |
| 9,901,754 | B2 | 2/2018 | Yamada |
| 9,949,785 | B2 | 4/2018 | Price et al. |
| 10,010,339 | B2 | 7/2018 | Witt et al. |
| 10,045,794 | B2 | 8/2018 | Witt et al. |
| 10,045,815 | B2 | 8/2018 | Tsubuku |
| 10,172,671 | B2 | 1/2019 | Masuda et al. |
| 10,245,065 | B2 | 4/2019 | Witt et al. |
| 10,265,094 | B2 | 4/2019 | Witt et al. |
| 10,357,273 | B2 | 7/2019 | Akagane |
| 10,433,865 | B2 | 10/2019 | Witt et al. |
| 10,433,866 | B2 | 10/2019 | Witt et al. |
| 10,433,896 | B2 | 10/2019 | Assmus et al. |
| 10,463,887 | B2 | 11/2019 | Witt et al. |
| 10,470,791 | B2 | 11/2019 | Houser |
| 10,575,895 | B2 | 3/2020 | Shelton, IV et al. |
| 10,610,286 | B2 | 4/2020 | Wiener et al. |
| 10,624,692 | B2 | 4/2020 | Akagane et al. |
| 10,631,861 | B2 | 4/2020 | Shelton, IV et al. |
| 10,660,692 | B2 | 5/2020 | Lesko et al. |
| 10,687,884 | B2 | 6/2020 | Wiener et al. |
| 10,688,321 | B2 | 6/2020 | Wiener et al. |
| 10,716,615 | B2 | 7/2020 | Shelton, IV et al. |
| 10,765,470 | B2 | 9/2020 | Yates et al. |
| 10,842,523 | B2 | 11/2020 | Shelton, IV et al. |
| 10,856,927 | B2 | 12/2020 | Lau et al. |
| 10,888,347 | B2 | 1/2021 | Witt et al. |
| 10,898,256 | B2 | 1/2021 | Yates et al. |
| 10,932,808 | B2 | 3/2021 | Shelton, IV et al. |
| 10,945,778 | B2 | 3/2021 | Weisenburgh, II et al. |
| 10,945,779 | B2 | 3/2021 | Weisenburgh, II et al. |
| 10,966,745 | B2 | 4/2021 | Akagane |
| 10,973,541 | B2 | 4/2021 | Madan et al. |
| 2005/0124987 | A1* | 6/2005 | Goble ................ A61B 18/1442 606/50 |
| 2007/0173872 | A1 | 7/2007 | Neuenfeldt |
| 2010/0145335 | A1 | 6/2010 | Johnson et al. |
| 2012/0150176 | A1 | 6/2012 | Weizman |
| 2014/0135804 | A1 | 5/2014 | Weisenburgh, II et al. |
| 2014/0330271 | A1 | 11/2014 | Dietz et al. |
| 2015/0148804 | A1 | 5/2015 | Rooks et al. |
| 2015/0164533 | A1 | 6/2015 | Felder et al. |
| 2015/0182251 | A1 | 7/2015 | Messerly et al. |
| 2016/0038220 | A1 | 2/2016 | Twomey |
| 2017/0007317 | A1 | 1/2017 | Allen, IV et al. |
| 2017/0105754 | A1 | 4/2017 | Boudreaux et al. |
| 2017/0164973 | A1 | 6/2017 | Lesko et al. |
| 2017/0202609 | A1 | 7/2017 | Shelton, IV et al. |
| 2019/0216491 | A1* | 7/2019 | Meiser ............... A61B 18/1442 |
| 2019/0216492 | A1 | 7/2019 | Meiser et al. |
| 2019/0216531 | A1 | 7/2019 | Van Tol et al. |
| 2021/0038292 | A1 | 2/2021 | Kabala et al. |

OTHER PUBLICATIONS

Invitation to Pay Additional Fees and Partial International Search Report received for PCT Patent Application No. PCT/IB2022/052156, mailed on Jun. 22, 2022, 12 pages.

* cited by examiner

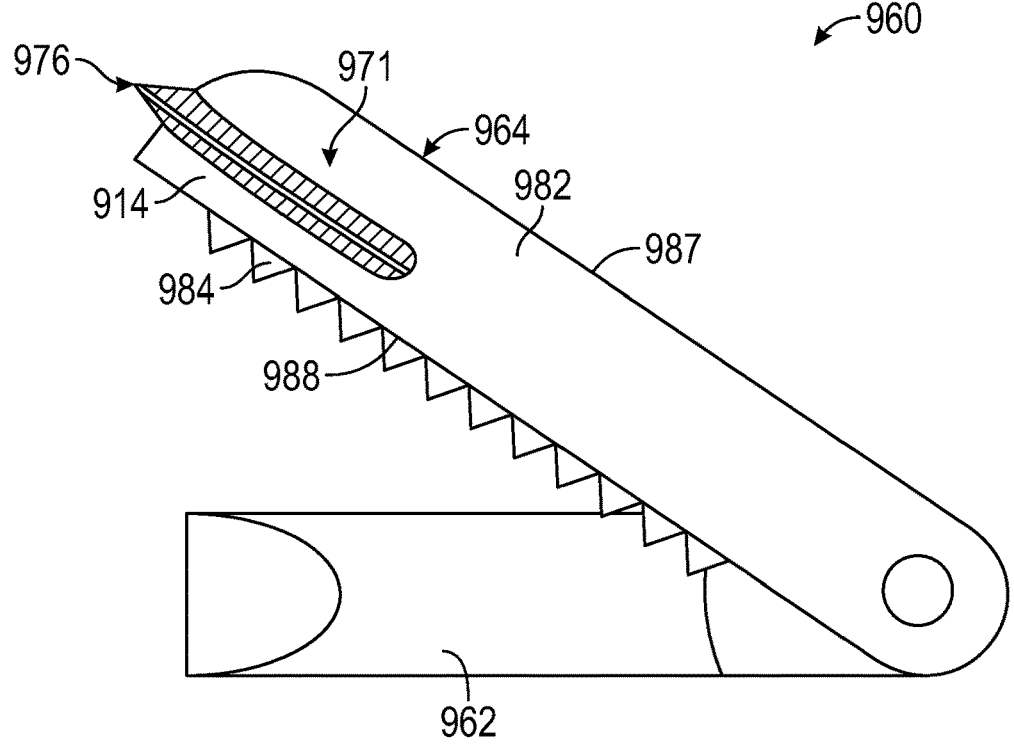
FIG. 9A
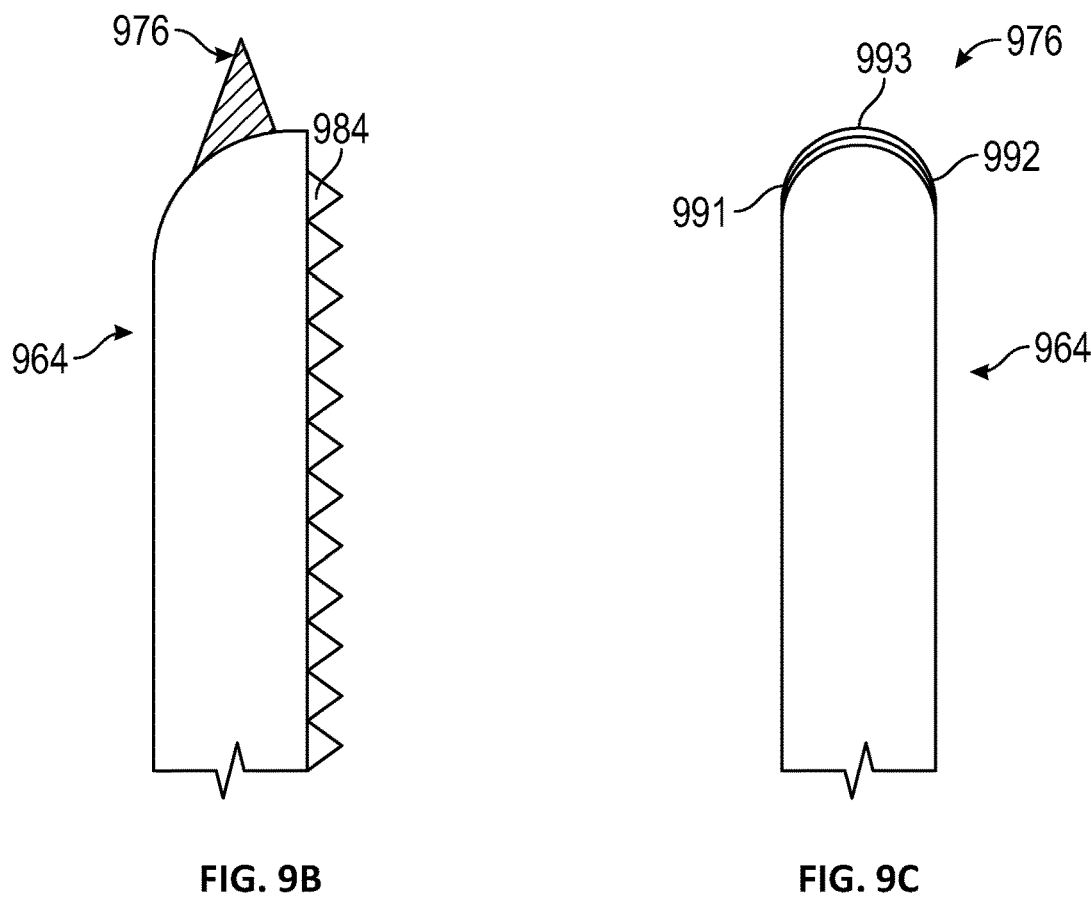
FIG. 9B                    FIG. 9C

SURGICAL INSTRUMENTS, SYSTEMS, AND METHODS INCORPORATING ULTRASONIC AND ELECTROSURGICAL FUNCTIONALITY

CROSS-REFERENCE TO RELATED APPLICATIONS

This application is a 371 National Stage Application of International Application No. PCT/IB2022/052156, filed Mar. 10, 2022, which claims the benefit of U.S. Provisional Patent Application No. 63/162,926, filed Mar. 18, 2021, the entire contents of each of which are hereby incorporated herein by reference.

FIELD

The present disclosure relates to energy-based surgical instruments and, more particularly, to surgical instruments, systems, and methods incorporating ultrasonic and electro-surgical functionality to facilitate energy-based tissue treatment.

BACKGROUND

Ultrasonic surgical instruments and systems utilize ultrasonic energy, i.e., ultrasonic vibrations, to treat tissue. More specifically, ultrasonic surgical instruments and systems utilize mechanical vibration energy transmitted at ultrasonic frequencies to treat tissue. An ultrasonic surgical device may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

Electrosurgical instruments and systems conduct Radio Frequency (RF) energy through tissue to treat tissue. An electrosurgical instrument or system may be configured to conduct bipolar RF energy between oppositely charged electrodes and through tissue, e.g., tissue clamped between the electrodes or otherwise in contact therewith, to treat tissue. Alternatively, or additionally, an electrosurgical instrument or system may be configured to deliver monopolar RF energy from an active electrode to tissue in contact with the electrode, with the energy returning via a remote return electrode device to complete the circuit.

SUMMARY

Provided in accordance with aspects of the disclosure is an end effector assembly of a surgical instrument including an ultrasonic blade adapted to receive ultrasonic energy to vibrate the ultrasonic blade. A jaw member is movable relative to the ultrasonic blade from a spaced-apart position to an approximated position for clamping tissue. The jaw member includes a structural body. The structural body defines a first side facing the ultrasonic blade and a second side facing away from the ultrasonic blade. A jaw liner is engaged with the first side of the structural body such that the jaw liner contacts the ultrasonic blade when the jaw member is in the approximated position. An electrode is engaged with the second side of the structural body. The electrode is adapted to connect to a source of electrosurgical energy. The electrode defines a first portion and a second portion. The first portion of the electrode is in contact with the structural body and the second portion of the electrode includes a taper defining an edge.

According to aspects of the disclosure, the ultrasonic blade and the electrode are independently energizable.

According to aspects of the disclosure, the electrode is a monopolar electrode.

According to aspects of the disclosure, the electrode defines a shark-fin shape.

According to aspects of the disclosure, the first portion of the electrode is embedded below the second side of the structural body.

According to aspects of the disclosure, the jaw liner is formed from an electrically-insulative material.

According to aspects of the disclosure, the jaw liner is formed from a more-compliant material and the structural body is formed from a more-rigid material.

According to aspects of the disclosure, the ultrasonic blade is adapted to connect to the source of electrosurgical energy at a potential different from a potential of the electrode.

Provided in accordance with aspects of the disclosure is a jaw member movable relative to the ultrasonic blade from a spaced-apart position to an approximated position for clamping tissue. The jaw member is movable from the approximated position to an over clamped position. A structural body includes an upper surface defining an opening facing away from the ultrasonic blade. The structural body defines a cavity aligned with the opening. A jaw liner is at least partially positioned in the cavity of the structural body. The jaw liner includes a first surface facing away from the ultrasonic blade and a second surface configured to contact the ultrasonic blade when the jaw member is in the approximated position. As the jaw member is moved from the approximated position to the over clamped position the jaw liner is forced vertically within the cavity. An electrode is adapted to connect to a source of electrosurgical energy. The electrode includes an upper portion facing away from the ultrasonic blade. The electrode is positioned on the first surface of the jaw liner such that as the jaw liner is forced vertically within the cavity the upper portion of the electrode projects through the opening of the structural body.

According to aspects of the disclosure, the jaw liner includes at least one arm projecting laterally within the cavity to movably secure the jaw liner in the cavity.

Provided in accordance with aspects of the disclosure is a structural body. The structural body defines a distal end. The structural body includes a lumen. The lumen defines an opening at the distal end of the structural body. A jaw liner is engaged with the structural body such that the jaw liner contacts the ultrasonic blade when the jaw member is in the approximated position. An electrode adapted to connect to a source of electrosurgical energy is extendably positioned in the lumen. The electrode defines a distal end. The distal end of the electrode is configured to project from the opening at the distal end of the structural body.

Provided in accordance with aspects of the disclosure is an electrode protruding from a distal end portion of a structural body. The electrode defines a curved shape having a first side portion, a second side portion opposite the first side portion and a distal-facing portion between the first side portion and the second side portion. The electrode defines an edge facing away from the structural body. The edge is configured to concentrate electrosurgical energy received from a source of electrosurgical energy.

According to aspects of the disclosure, the ultrasonic blade and the jaw member are configured to be rotated by a rotation knob to treat tissue with the edge of the electrode.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 9A is a side view of another end effector assembly in accordance with the present disclosure;

FIG. 9B is a cross-sectional view of a jaw member of the end effector assembly of FIG. 9A; and FIG. 9C is a top plan view of the jaw member of the end effector assembly of FIG. 9A.

DETAILED DESCRIPTION

Figure 1:
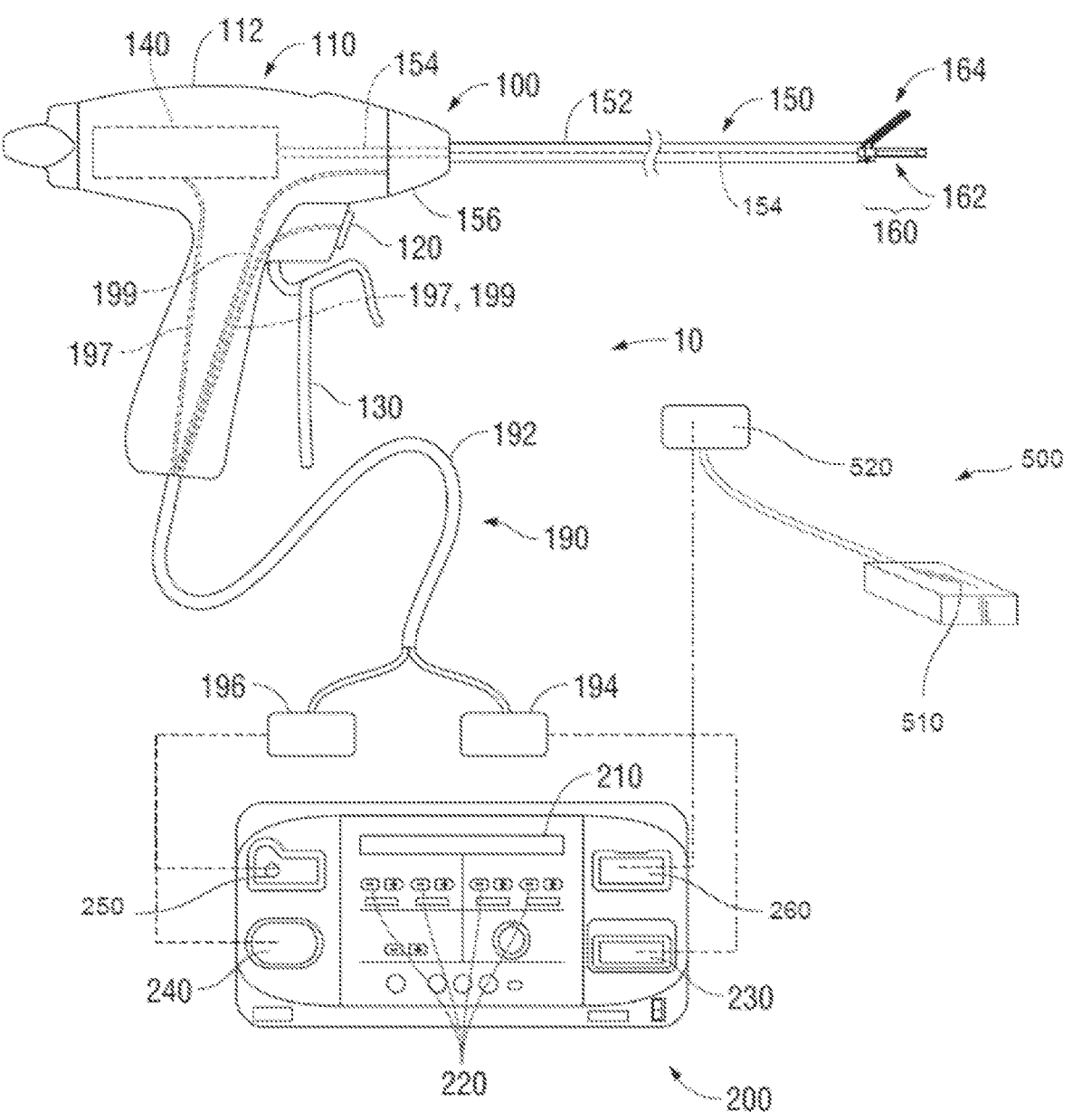
FIG. 1 illustrates a surgical system provided in accordance with the present disclosure including a surgical instrument, a surgical generator and, in some aspects, a return electrode device.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Referring to FIG. 1, a surgical system provided in accordance with aspects of the present disclosure is shown generally identified by reference numeral 10 including a surgical instrument 100, a surgical generator 200, and, in some aspects, a return electrode device 500, e.g., including a return pad 510. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200. As an alternative to handle assembly 110, surgical instrument 100 may include a robotic attachment housing for releasable engagement with a robotic arm of a robotic surgical system such as, for example, robotic surgical system 1000 (FIG. 2) detailed below.

Surgical generator 200 includes a display 210, a plurality user interface features 220, e.g., buttons, touch screens, switches, etc., an ultrasonic plug port 230, a bipolar electrosurgical plug port 240, and active and return monopolar electrosurgical plug ports 250, 260, respectively. Surgical generator 200 is configured to produce ultrasonic drive signals for output through ultrasonic plug port 230 to surgical instrument 100 to activate surgical instrument 100 in an ultrasonic mode and to provide electrosurgical energy, e.g., RF bipolar energy, for output through bipolar electrosurgical plug port 240 and/or RF monopolar energy for output through active monopolar electrosurgical port 250 to surgical instrument 100 to activate surgical instrument 100 in one or more electrosurgical modes. It is also contemplated that one or more common ports (not shown) may be configured to act as any two or more of ports 230-260. In monopolar configurations, plug 520 of return electrode device 500 is configured to connect to return monopolar electrosurgical plug port 260.

Continuing with reference to FIG. 1, handle assembly 110 includes a housing 112 defining a body portion and a fixed handle portion. Handle assembly 110 further includes an activation button 120 and a clamp trigger 130. Multiple activation buttons 120 may be positioned about handle assembly 110 to activate ultrasonic energy or electrosurgical energy, as described herein. The body portion of housing 112 is configured to support an ultrasonic transducer 140. Ultrasonic transducer 140 may be permanently engaged with the body portion of housing 112 or removable therefrom. Ultrasonic transducer 140 includes a piezoelectric stack or other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting and a second actuated position corresponding to a second activation setting. In still other configurations, separate activation buttons may be provided, e.g., a first actuation button for activating a first activation setting and a second activation button for activating a second activation setting.

Elongated assembly 150 of surgical instrument 100 includes an outer drive sleeve 152, an inner support sleeve 153 (FIG. 3) disposed within outer drive sleeve 152, a waveguide 154 extending through inner support sleeve 153 (FIG. 3), a drive assembly (not shown), a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164 and a distal end of inner support sleeve 153 (FIG. 3) pivotably supports jaw member 164. As such, clamp trigger 130 is selectively actuatable to thereby move outer drive sleeve 152 about inner support sleeve 153 (FIG. 3) to pivot jaw member 164 relative to blade 162 of end effector assembly 160 from a spaced apart position to an approximated position for clamping tissue between jaw member 164 and blade 162. The configuration of outer and inner sleeves 152, 153 (FIG. 3) may be reversed, e.g., wherein outer sleeve 152 is the support sleeve and inner sleeve 153 (FIG. 3) is the drive sleeve. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Waveguide 154, as noted above, extends from handle assembly 110 through the inner support sleeve. Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although nonconductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that, as detailed below, bipolar electrosurgical energy may be conducted between blade 162 and jaw member 164 (and/or between different portions of jaw member 164). In monopolar configurations, an electrical lead wire 199 is electrically coupled to waveguide 154 such that, as also detailed below, monopolar electrosurgical energy may be supplied to tissue from blade 162. Alternatively, an electrical lead wire 199 may electrically couple to jaw member 164 in the monopolar configuration to enable monopolar electrosurgical energy to be supplied to tissue from jaw member 164. One or more second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated.

Figure 2:
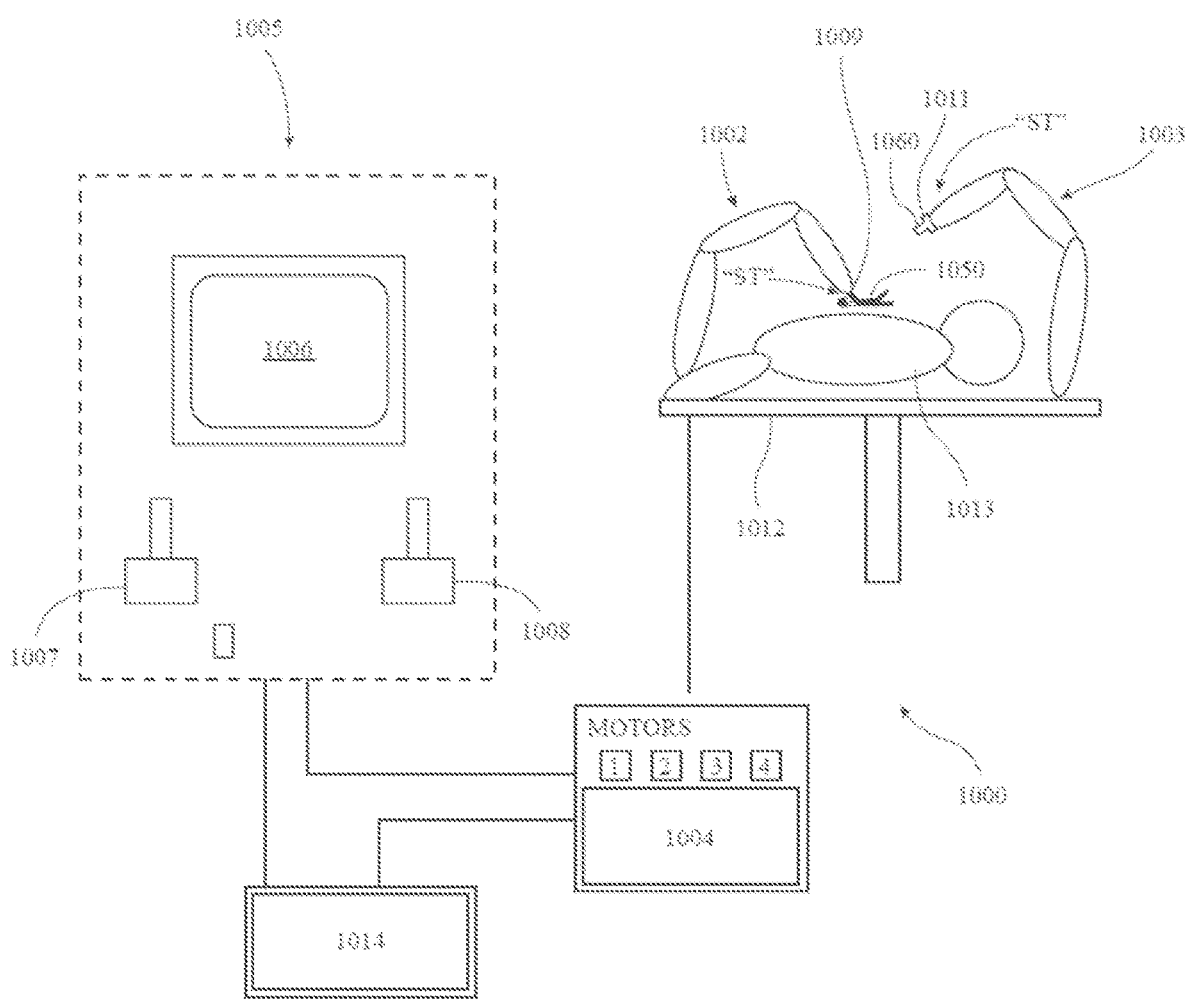
FIG. 2 is a schematic illustration of a robotic surgical system provided in accordance with the present disclosure.

With reference to FIG. 2, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be ultrasonic surgical instrument 100 (FIG. 1), e.g., configured for use in both an ultrasonic mode and an electrosurgical (bipolar and/or monopolar) mode, wherein manual actuation features, e.g., actuation button 120 (FIG. 1), clamp lever 130 (FIG. 1), etc., are replaced with robotic inputs. In such configurations, robotic surgical system 1000 may include or be configured to connect to an ultrasonic generator, an electrosurgical generator, and/or a power source. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 3:
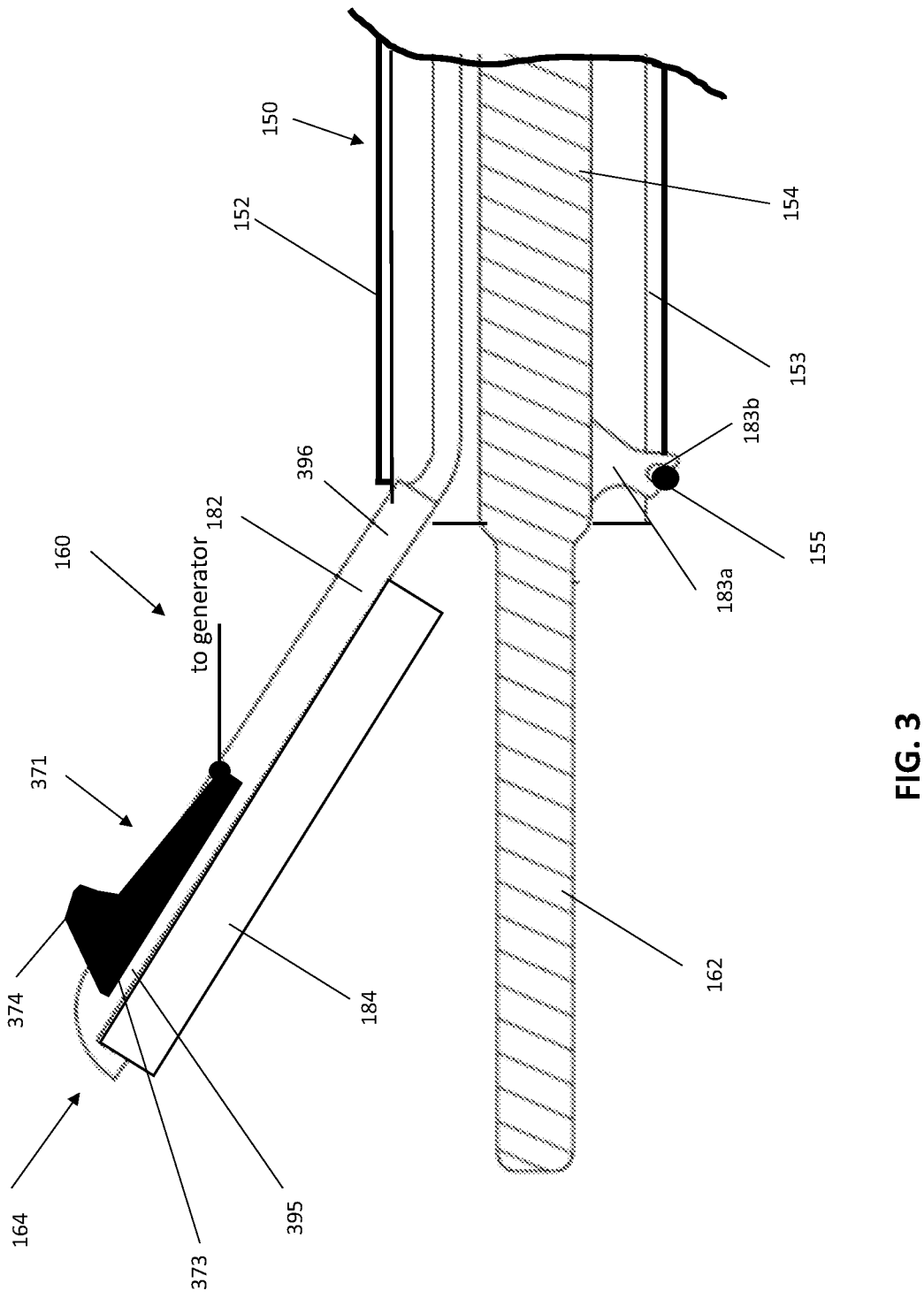
FIG. 3 is a longitudinal cross-sectional view of an end effector assembly of the surgical instrument of FIG. 1.

Referring to FIG. 3, end effector assembly 160 of surgical instrument 100 of surgical system 10 (FIG. 1) is detailed, although end effector assembly 160 may be utilized with any other suitable surgical instrument and/or surgical system. End effector assembly 160 includes a blade 162 and a jaw member 164. Blade 162 may define a linear configuration, may define a curved configuration, or may define any other suitable configuration, e.g., straight and/or curved surfaces, portions, and/or sections; one or more convex and/or concave surfaces, portions, and/or sections; etc. With respect to curved configurations, blade 162, more specifically, may be curved in any direction relative to jaw member 164, for example, such that the distal tip of blade 162 is curved towards jaw member 164, away from jaw member 164, or laterally (in either direction) relative to jaw member 164. Further, blade 162 may be formed to include multiple curves in similar directions, multiple curves in different directions within a single plane, and/or multiple curves in different directions in different planes. In addition, blade 162 may additionally or alternatively be formed to include any suitable features, e.g., a tapered configuration, various different cross-sectional configurations along its length, cut outs, indents, edges, protrusions, straight surfaces, curved surfaces, angled surfaces, wide edges, narrow edges, and/or other features.

Figure 5:
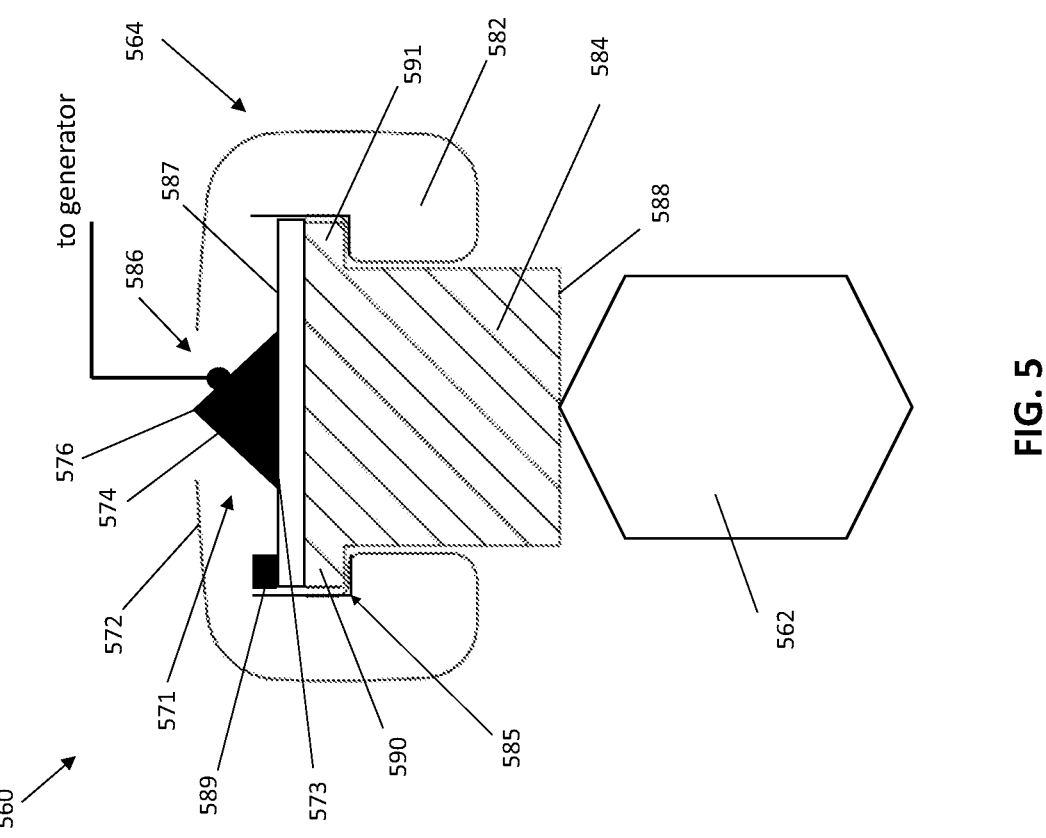

Blade 162 may define a polygonal, rounded polygonal, or any other suitable cross-sectional configuration(s) (see FIG. 5). Waveguide 154 or at least the portion of waveguide 154 proximally adjacent blade 162, may define a cylindrical shaped configuration. Plural tapered surfaces (not shown) may interconnect the cylindrically shaped waveguide 154 with the polygonal (rounded edge polygonal, or other suitable shape) configuration of blade 162 to define smooth transitions between the body of waveguide 154 and blade 162.

Blade 162 may be wholly or selectively coated with a suitable material, e.g., a non-stick material, an electrically insulative material, an electrically conductive material, combinations thereof, etc. Suitable coatings and/or methods of applying coatings include but are not limited to Teflon®, polyphenylene oxide (PPO), deposited liquid ceramic insulative coatings; thermally sprayed coatings, e.g., thermally sprayed ceramic; Plasma Electrolytic Oxidation (PEO) coatings; anodization coatings; sputtered coatings, e.g.; silica; Electro Bond® coating available from Surface Solutions Group of Chicago, IL, USA; or other suitable coatings and/or methods of applying coatings.

Figure 4:
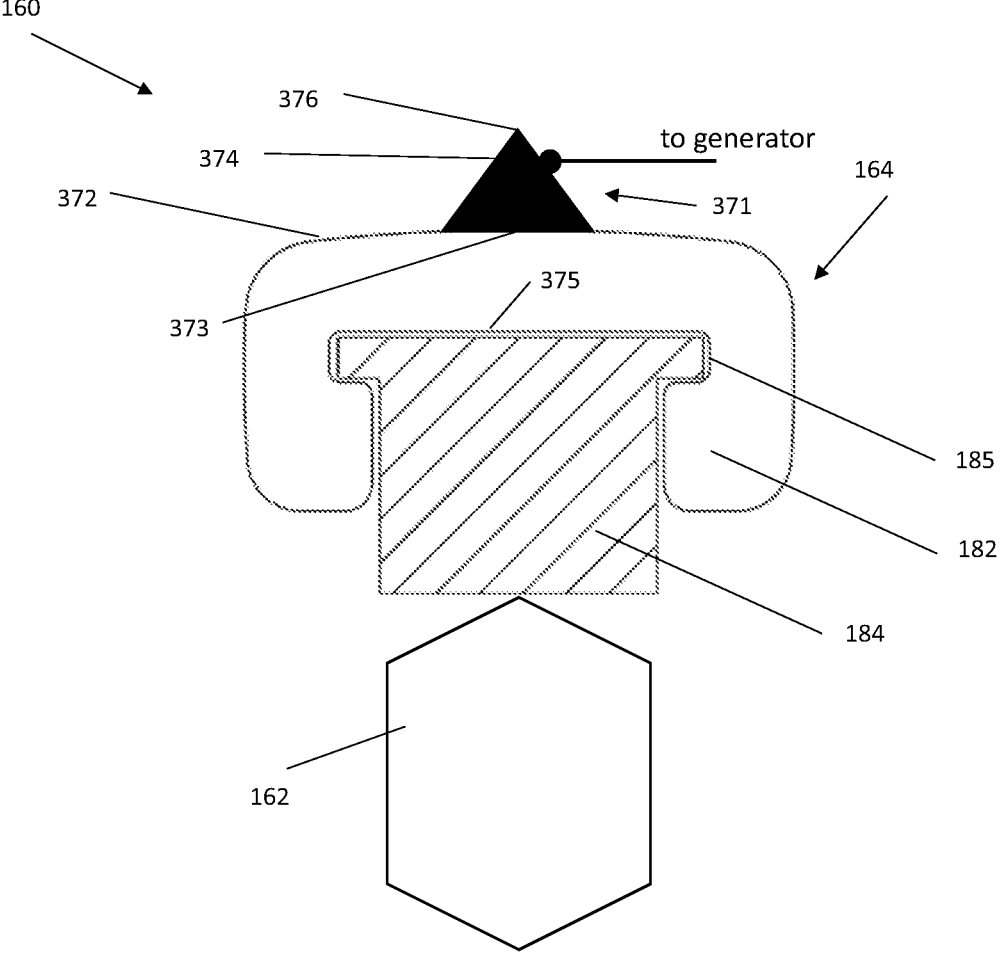
FIG. 4 is a transverse cross-sectional view of the end effector assembly of FIG. 3.

With additional reference to FIGS. 4 and 5, blade 162, as noted above, in addition to receiving ultrasonic energy transmitted along waveguide 154 from ultrasonic transducer 140 (FIG. 1), is adapted to connect to generator 200 (FIG. 1) to enable the supply of RF energy to blade 162 for conduction to tissue in contact therewith. In bipolar configurations, RF energy is conducted between blade 162 and jaw member 164 (or between portions of jaw member 164 and/or blade 162) and through tissue disposed therebetween to treat tissue. In monopolar configurations, RF energy is conducted from blade 162, serving as the active electrode, to tissue in contact therewith and is ultimately returned to generator 200 (FIG. 1) via return device 500 (FIG. 1), serving as the passive or return electrode. Alternatively, jaw member 164 (or portions thereof) may be energizable in the monopolar configuration while blade 162 is unenergized.

Jaw member 164 of end effector assembly 160 includes a more rigid structural body 182 and a more compliant jaw liner 184. Structural body 182 may be formed from an electrically conductive material, e.g., stainless steel, and/or may include electrically conductive portions. Structural body 182 includes a pair of proximal flanges 183a that are pivotably coupled to the inner support sleeve 153 via receipt of pivot bosses (not shown) of proximal flanges 183a within corresponding openings (not shown) defined within the inner support sleeve 153 and operably coupled with outer drive sleeve 152 via a drive pin 155 secured relative to outer drive sleeve 152 and pivotably received within apertures 183b defined within proximal flanges 183a. As such, sliding of outer drive sleeve 152 about inner support sleeve 153 pivots jaw member 164 relative to blade 162 from a spaced apart position to an approximated position to clamp tissue between jaw liner 184 of jaw member 164 and blade 162.

Structural body 182, or a portion(s) thereof, may be adapted to connect to a source of electrosurgical energy, e.g., generator 200 (FIG. 1), and, in a bipolar electrosurgical mode, is charged to a different potential as compared to blade 162 to enable the conduction of bipolar electrosurgical (e.g., RF) energy through tissue clamped therebetween, to treat the tissue. In a monopolar electrosurgical mode, structural body 182 may be un-energized, may be charged to the same potential as compared to blade 162 (thus both defining the active electrode), or may be energized while blade 162 is not energized (wherein structural body 182 defines the active electrode). In either monopolar configuration, energy is returned to generator 200 (FIG. 1) via return device 500 (FIG. 1), which serves as the passive or return electrode.

Jaw liner 184 is shaped complementary to a cavity 185 (FIG. 4) defined within structural body 182, e.g., defining a T-shaped configuration, to facilitate receipt and retention therein, although other configurations are also contemplated. Jaw liner 184 is fabricated from an electrically insulative, compliant material such as, for example, polytetrafluoroethylene (PTFE). The compliance of jaw liner 184 enables blade 162 to vibrate while in contact with jaw liner 184 without damaging components of ultrasonic surgical instrument 100 (FIG. 1) and without compromising the hold on tissue clamped between jaw member 164 and blade 162. Jaw liner 184 extends from structural body 182 towards blade 162 to inhibit contact between structural body 182 and blade 162 in the approximated position of jaw member 164. The insulation of jaw liner 184 maintains electrical isolation between blade 162 and structural body 182 of jaw member 164, thereby inhibiting shorting.

As detailed above, structural body 182 may be adapted to connect to a source of electrosurgical energy, e.g., generator 200 (FIG. 1), and, in a bipolar electrosurgical mode, is charged to a different potential as compared to blade 162 to enable the conduction of bipolar electrosurgical (e.g., RF) energy through tissue clamped therebetween, to treat, e.g., seal, the tissue. Additionally or alternatively, the distal portion of end effector assembly 160 (acting as a probe with jaw member 164 in the approximated position without tissue therebetween) may be advanced distally into and/or moved transversely across tissue such that tissue (and/or a conductive medium such as saline) contacts and electrically connects the distal face of blade 162 and a distal cap portion of structural body 182 to enable the conduction of bipolar electrosurgical (e.g., RF) energy through the tissue to treat or interrogate, e.g., spot coagulate, cut, or otherwise treat, the tissue.

According to aspects of the disclosure, structural body 182 includes an electrode 371. The electrode 371 is adapted to connect to generator 200 (FIG. 1) to enable the supply of RF energy to electrode 371 for conduction to tissue in contact therewith. In bipolar configurations, RF energy is conducted between ultrasonic blade 162 and electrode 371, between electrode 371 and structural body 182, or between portions of one or more of blade 162, electrode 371, and/or structural body 182 to treat tissue. In these and/or other aspects, electrode 371 is electrically isolated from structural body 182, e.g., via an insulative material disposed therebetween. The insulative material may be employed in either monopolar or bipolar configurations. In monopolar configurations, RF energy is conducted from electrode 371, serving as the active electrode, to tissue in contact therewith and is ultimately returned to generator 200 (FIG. 1) via return device 500 (FIG. 1), serving as the passive or return electrode.

The ultrasonic blade 162, the structural body 182, and/or the electrode 371 may be independently energizable. In aspects, one or more of the ultrasonic blade 162, the structural body 182, and/or the electrode 371 may be energized to the same or different potentials or may be un-energized.

Referring particularly to FIGS. 3 and 4, end effector assembly 160 is described in accordance with configurations of the present disclosure. The end effector assembly 160 includes the ultrasonic blade 162 adapted to receive ultrasonic energy to vibrate the ultrasonic blade 162. The jaw member 164 is movable relative to the ultrasonic blade 162 from a spaced-apart position to an approximated position for clamping tissue. The jaw member 164 includes the structural body 182. The structural body 182 defines a first side 375 facing the ultrasonic blade 162 and a second side 372 facing away from the ultrasonic blade 162. A jaw liner 184 is engaged with the first side 375 of the structural body 182 such that the jaw liner 184 contacts the ultrasonic blade 162 when the jaw member 164 is in the approximated position. The electrode 371 is engaged with the second side 372 of the structural body 182. The electrode 371 is adapted to connect to a source of electrosurgical energy, as described herein.

The electrode 371 has a shark-fin like shape in which a lower portion 373 of electrode 371 is relatively longer than the upper portion 374 of the electrode 371. As an example, the upper portion 374 of electrode 371 may define a substantially flat shape (e.g., a continuously flat upper surface) along a length thereof. Alternatively, the electrode 371 may define a curved upper portion 374. At least a portion of the electrode 371 may have a substantially triangular shape when viewed in cross-section (see, e.g., FIG. 4) in which the upper portion 374 of electrode 371 tapers to an edge 376. Edge 376 may be a pointed edge; however, a flat edge having a blunt configuration may also be employed. The pointed edge 376 extends from the distal end portion 395 of structural body 182 toward the proximal end portion 396 of structural body 182. A height of the electrode 371 with respect to the upper surface 371 of the structural body 182 may vary along the upper portion 374 of the electrode 371.

In aspects of the disclosure, the electrode 371 may be at least partially embedded in structural body 182 such that a lower portion 373 of electrode 371 is positioned below the upper surface 372 of structural body 182 and an upper portion 374 of electrode 371 including pointed edge 376 projects above the upper surface 372 of structural body 182. The electrode 371 is positioned at the distal end portion 395 of structural body 182 opposite the proximal end portion 396 of structural body 182.

According to aspects of the disclosure, the jaw liner 184 is formed from an electrically-insulative material. As an example, the jaw liner 184 is formed from a more-compliant material and the structural body 182 is formed from a more-rigid material.

Figure 6:
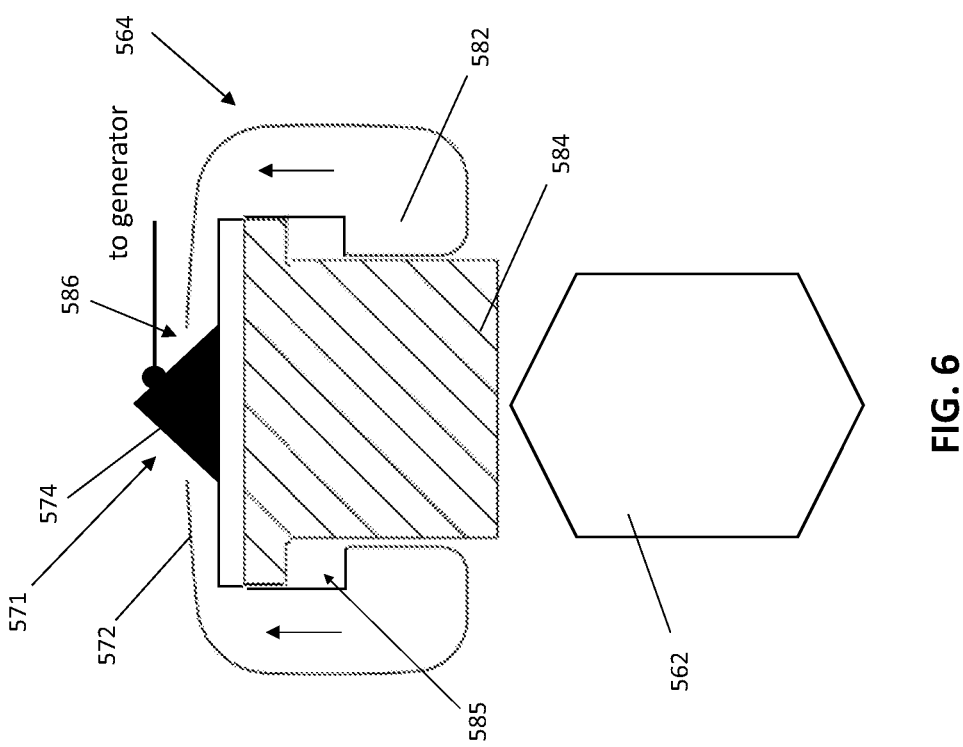
FIGS. 5 and 6 are transverse cross-sectional views of another end effector assembly in accordance with the present disclosure with a monopolar element in a retracted and extended position, respectively.

Referring to FIGS. 5 and 6, another end effector assembly 560 for a surgical instrument includes a jaw member 564 and an electrode 571 adapted to connect to a source of electrosurgical energy. As an example, electrode 571 may include a lower portion 573 and an upper portion 574 tapering to a pointed edge 576. End effector assembly 560 may be utilized with any of the instruments above or any other suitable instrument. Further, to the extent consistent, any of the aspects and/or features of any of the other end effector assemblies detailed herein may be utilized with end effector assembly 560 and vice versa.

The jaw member 564 of the end effector assembly 560 includes a structural body 582. The structural body 582 includes an upper surface 572 defining an opening 586 facing away from the ultrasonic blade 562. The structural body 582 defines a cavity 585 aligned with (e.g., vertically aligned with) the opening 586.

A jaw liner 584 is at least partially movably positioned in the cavity 585 of the structural body 582. The jaw liner 584 may include arms 590 and 591 to movably secure the jaw liner 584 in cavity 585.

The jaw liner 584 includes a first surface 587 facing away from the ultrasonic blade 562 and a second surface 588 configured to contact the ultrasonic blade 562 when the jaw member 564 is in the approximated position (see, e.g., FIG. 5), such that as the jaw member 564 is moved from the approximated position to an over clamped position (see, e.g., FIG. 6) the jaw liner 584 is forced vertically within cavity 585.

The electrode 571 is positioned on the first surface 587 of the jaw liner 584 such that as the jaw liner 584 is forced vertically within the cavity the upper portion 574 of the electrode 571 projects through the opening 586 of the structural body 582 (see, e.g., FIG. 6). In use, the jaw liner 584 may be forced vertically through contact with the ultrasonic blade 562 by over clamping the jaw member 564. While tissue may be positioned between the jaw liner 584 and the ultrasonic blade 562 during over clamping, the presence of tissue is not required, and the jaw member 564 may be over clamped to expose the upper portion 574 of electrode 571 when tissue is not present between the jaw liner 584 and the ultrasonic blade 562.

The jaw liner 584 may be biased towards the ultrasonic blade 562 (e.g., by at least one spring 589 positioned in cavity 585).

Figure 8:
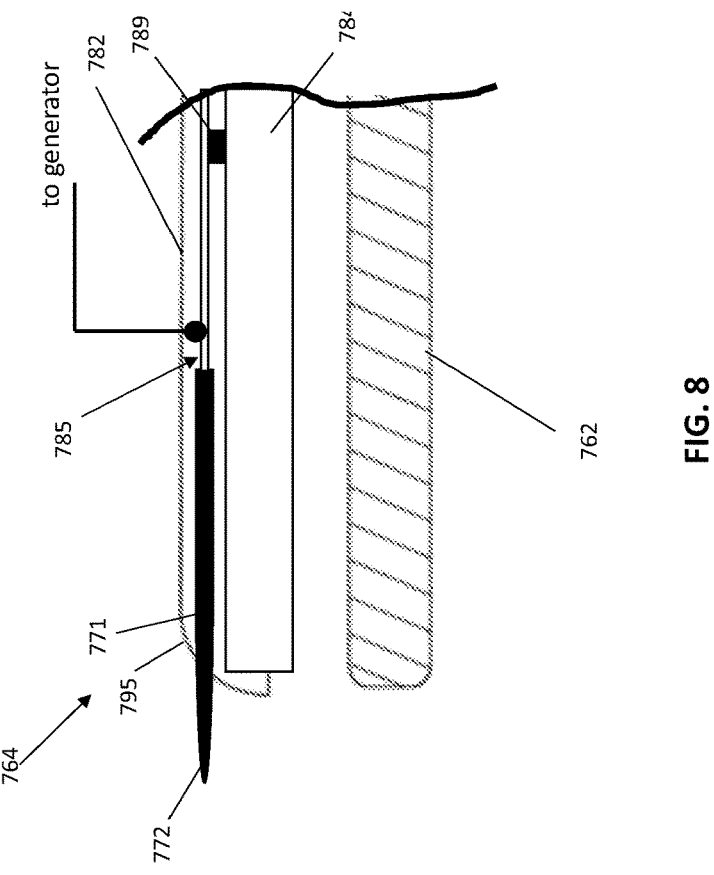
FIGS. 7 and 8 are longitudinal cross-sectional views of another end effector assembly in accordance with the present disclosure with a monopolar element in a retracted and extended position, respectively.
Figure 7:
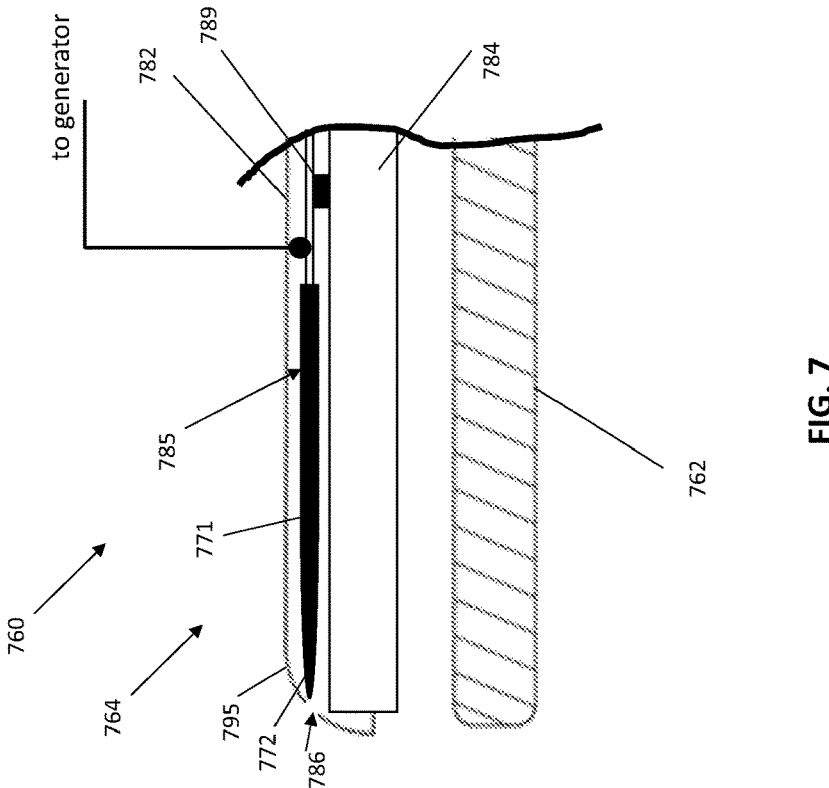

Referring to FIGS. 7 and 8, another end effector assembly 760 for a surgical instrument including a jaw member 764 having a structural body 782 and a jaw liner 784, an ultrasonic blade 762 and an electrode 771 adapted to connect to a source of electrosurgical energy is described. End effector assembly 760 may be utilized with any of the instruments above or any other suitable instrument. Further, to the extent consistent, any of the aspects and/or features of any of the other end effector assemblies detailed herein may be utilized with end effector assembly 760 and vice versa.

The structural body 782 defines a distal end 795. The structural body 782 includes a lumen 785. The lumen 785 defines an opening 786 at the distal end 795 of the structural body 782. The jaw liner 784 is engaged with the structural body 782 such that the jaw liner 784 contacts the ultrasonic blade 762 when the jaw member 764 is in the approximated position. An electrode 771 adapted to connect to a source of electrosurgical energy is extendably positioned in the lumen 785. The electrode 771 defines a distal end 772. The distal end 772 of the electrode 771 is configured to project from the opening 786 at the distal end 795 of the structural body 782 (e.g., when the electrode 771 is in use).

The electrode 771 may be biased (e.g., by spring 789) to be positioned completely within lumen 185 when not in use. When in use, the electrode 771 may be advanced (e.g., manually advanced or electronically advanced such as by a motor) to expose the distal end 772 of the electrode 771 to tissue. When released, the spring 789 forces the electrode 771 back into the lumen 785. As an example, the electrode 771 may be advanced by over clamping jaw 784.

Referring to FIGS. 9A, 9B and 9C, another end effector assembly 960 for a surgical instrument including a jaw member 964 having a structural body 982 and a jaw liner 984, an ultrasonic blade 962 and an electrode 971 adapted to connect to a source of electrosurgical energy is described. End effector assembly 960 may be utilized with any of the instruments above or any other suitable instrument. Further, to the extent consistent, any of the aspects and/or features of any of the other end effector assemblies detailed herein may be utilized with end effector assembly 960 and vice versa.

The electrode 971 protrudes from a distal end portion 914 of the structural body 982 between a first side 987 and a second side 988 of the structural body 982. The electrode 971 defines a curved shape (see, e.g., FIG. 9C) having a first side portion 991, a second side portion 992 opposite the first side portion 991 and a distal-facing portion 993 between the first side portion 991 and the second side portion 992. The electrode 971 defines an edge 976 facing away from the structural body 982. The edge 976 is configured to concentrate electrosurgical energy received from a source of electrosurgical energy. The electrode 971 may taper such that edge 976 defines a pointed end facing away the structural body 982. The shape of electrode 971 defines an edge 976 that is monopolar sharp by concentrating electrosurgical energy, but is physically dull. This arrangement allows for precise tissue treatment (e.g., dissection) at a reduced electrosurgical energy power level.

According to aspects of the disclosure, the end effector assembly 960 including the ultrasonic blade 962 and the jaw member 964 are configured to be rotated by a rotation knob (e.g., rotation knob 156) to treat tissue with the edge 976 of the electrode 971. As an example, the end effector assembly 960 may be rotated about 90 degrees to treat tissue.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An end effector assembly of a surgical instrument, comprising:
    an ultrasonic blade adapted to receive ultrasonic energy to vibrate the ultrasonic blade; and
    a jaw member movable relative to the ultrasonic blade from a spaced-apart position to an approximated position for clamping tissue therebetween, the jaw member further movable from the approximated position to an over clamped position, the jaw member including:

a structural body, the structural body including an upper surface defining an opening facing away from the ultrasonic blade, the structural body defining a cavity aligned with the opening;
        a jaw liner at least partially positioned in the cavity of the structural body, the jaw liner including a first surface facing away from the ultrasonic blade and a second surface configured to contact the ultrasonic blade when the jaw member is in the approximated position, such that as the jaw member is moved from the approximated position to the over clamped position, the jaw liner is forced vertically within the cavity; and
        an electrode adapted to connect to a source of electrosurgical energy, the electrode including an upper portion facing away from the ultrasonic blade, the electrode positioned on the first surface of the jaw liner such that as the jaw liner is forced vertically within the cavity the upper portion of the electrode projects through the opening of the structural body.

2. The end effector assembly according to claim 1, wherein the ultrasonic blade and the electrode are independently energizable.

3. The end effector assembly according to claim 1, wherein the electrode is a monopolar electrode.

4. The end effector assembly according to claim 1, wherein the electrode defines a shark-fin shape.

5. The end effector assembly according to claim 1, wherein the jaw liner is formed from a compliant material and the structural body is formed from a rigid material.

6. The end effector assembly according to claim 5, wherein the jaw liner is formed from an electrically-insulative material.

7. The end effector assembly according to claim 1, wherein the ultrasonic blade is adapted to connect to the source of electrosurgical energy at a potential different from a potential of the electrode.

8. The end effector assembly according to claim 1, wherein the electrode includes a lower portion, and wherein the upper portion tapers to a pointed edge.

9. The end effector assembly according to claim 1, wherein the jaw liner is biased towards the ultrasonic blade by at least one spring.

10. The end effector assembly according to claim 1, wherein the jaw liner includes a first arm and a second arm.

11. The end effector assembly according to claim 10, wherein the first arm and the second arm contact a first inner surface and a second inner surface, respectively, of the structural body when in the approximated position, and wherein the first arm and the second arm are spaced from the first inner surface and the second inner surface when in the over clamped position.

12. The end effector assembly according to claim 11, wherein, when in the over clamped position, the cavity comprises a first portion and a second portion, wherein the first portion is defined, at least in part, by the first arm and the first inner surface, and the second portion is defined, at least in part, by the second arm and the second inner surface.

13. The end effector assembly according to claim 1, wherein the electrode is at least partially embedded in the structural body such that a lower portion of the electrode is positioned below the upper surface of the structural body and the upper portion of the electrode includes a pointed edge that projects above the upper surface of the structural body, when in the over clamped position.

\* \* \* \* \*